US00PP18575P3

(12) United States Plant Patent
Amorao et al.

(10) Patent No.: US PP18,575 P3
(45) Date of Patent: Mar. 11, 2008

(54) STRAWBERRY PLANT NAMED 'DRISCOLL OJAI'

(50) Latin Name: *Fragaria×ananassa*
Varietal Denomination: Driscoll Ojai

(75) Inventors: Amado Amorao, Camarillo, CA (US); Michael Ferguson, Moorpark, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 32 days.

(21) Appl. No.: 11/244,121

(22) Filed: Oct. 4, 2005

(65) Prior Publication Data

US 2007/0079406 P1 Apr. 5, 2007

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner*—Kent Bell

(74) *Attorney, Agent, or Firm*—Jones Day

(57) ABSTRACT

This invention relates to a new and distinct variety of strawberry named 'Driscoll Ojai'. The variety is similar to the varieties 'Driscoll El Capitan' and 'Driscoll Venice'. The variety is distinguished from 'Driscoll El Capitan' and 'Driscoll Venice,' in particular, by its height, longer petiole length, longer fruiting truss length, open canopy density and moderate susceptibility to powdery mildew.

5 Drawing Sheets

Latin name of the genus and species of the plant claimed: The variety is botanically identified as *Fragaria×ananassa.*

Variety Denomination: The strawberry variety denomination is 'Driscoll Ojai'.

BACKGROUND OF THE INVENTION

The new variety originated as a result of a controlled cross between male cultivar 'Driscoll El Capitan' (U.S. Plant Pat. No. PP 14,005) and female cultivar 'Driscoll Venice' (U.S. Plant Pat. No. PP 14,062) in an ongoing breeding program, and was discovered as a seedling in Ventura County, Calif. in 1999. The original seedling of the new cultivar was asexually propagated by stolons in a Nursery in Shasta County, Calif. Propagules were transplanted to a controlled breeding plot in Ventura County, Calif., where the variety was identified and selected for further evaluation. 'Driscoll Ojai' was subsequently asexually propagated and underwent further testing in Ventura County, Calif. for four years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Driscoll Ojai'. The variety is botanically identified as *Fragaria×ananassa.* The new variety is distinguished from other varieties by a number of characteristics as set forth in Tables 1–4.

COMPARISON TO SIMILAR VARIETIES

The varieties which we believe to be similar to 'Driscoll Ojai' from those known to us are 'Driscoll El Capitan' (U.S. Plant Pat. No. PP 14,005) and 'Driscoll Venice' (U.S. Plant Pat. No. PP 14,062). There are several characteristics of the new variety that are different from, or not possessed by 'Driscoll El Capitan' and 'Driscoll Venice'. For example, the new variety is taller, has a longer petiole length, a longer fruiting truss length, an open canopy density and is moderately susceptible to powdery mildew. Additional characteristics of 'Driscoll Ojai' include a strong sweetness with a seasonal average brix of 9.3. Furthermore, additional petal characteristics of 'Dricoll Ojai' include an orbicular petal shape, a rounded petal apex, an entire petal margin, a concavo-convex petal base and a typical and observed petal number of 5. Additional sepal characteristics of 'Driscoll Ojai' include an elliptic sepal shape and a typical and observed sepal number of 10. The sepal apex of 'Driscoll Ojai' can be either convex or complex and the sepal margin of 'Driscoll Ojai' can be either entire or serrate. Additional leaf characteristics of 'Driscoll Ojai' include a typical and observed rounded leaflet shape and a rounded leaf apex.

'Driscoll Ojai' is distinguished from its parent, 'Driscoll El Capitan' and 'Driscoll Venice' as indicated in Tables 1–4.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
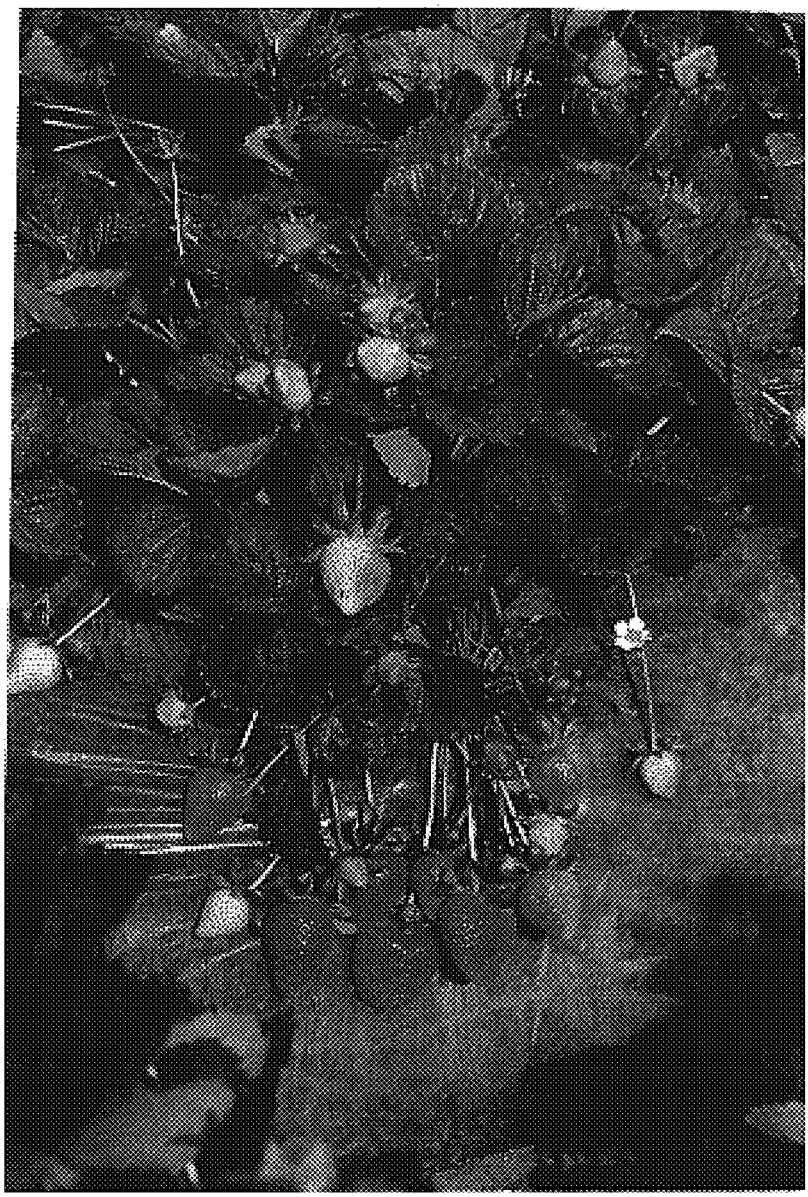
FIG. 1 shows the whole the plant.
Figure 2:
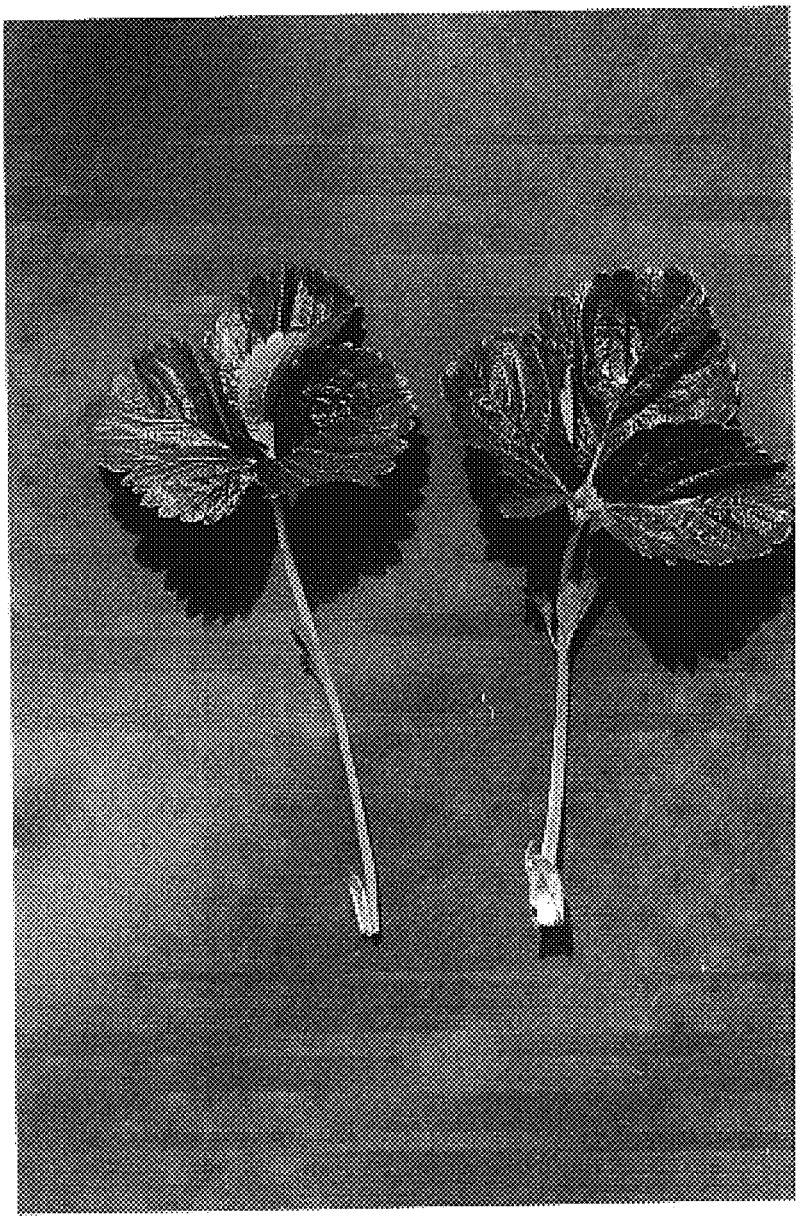
FIG. 2 shows the upper side of the leaves of the plant.
Figure 3:
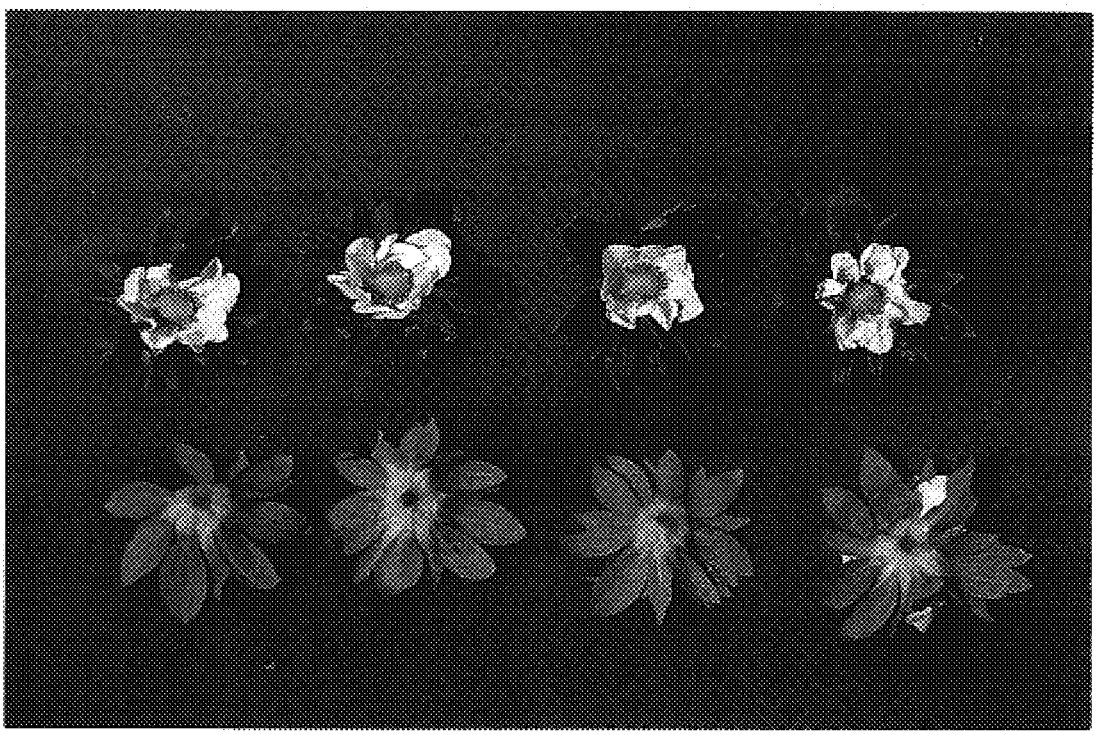
FIG. 3 shows the under side and upper side of the flowers.
Figure 4:
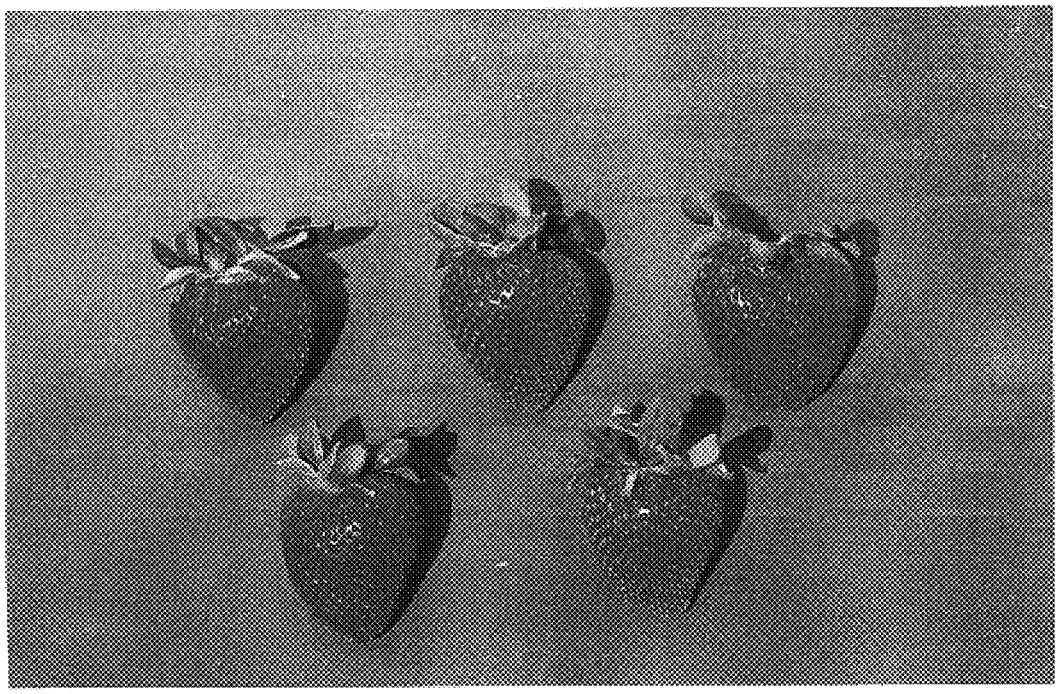
FIG. 4 shows a close-up of the fruit.
Figure 5:
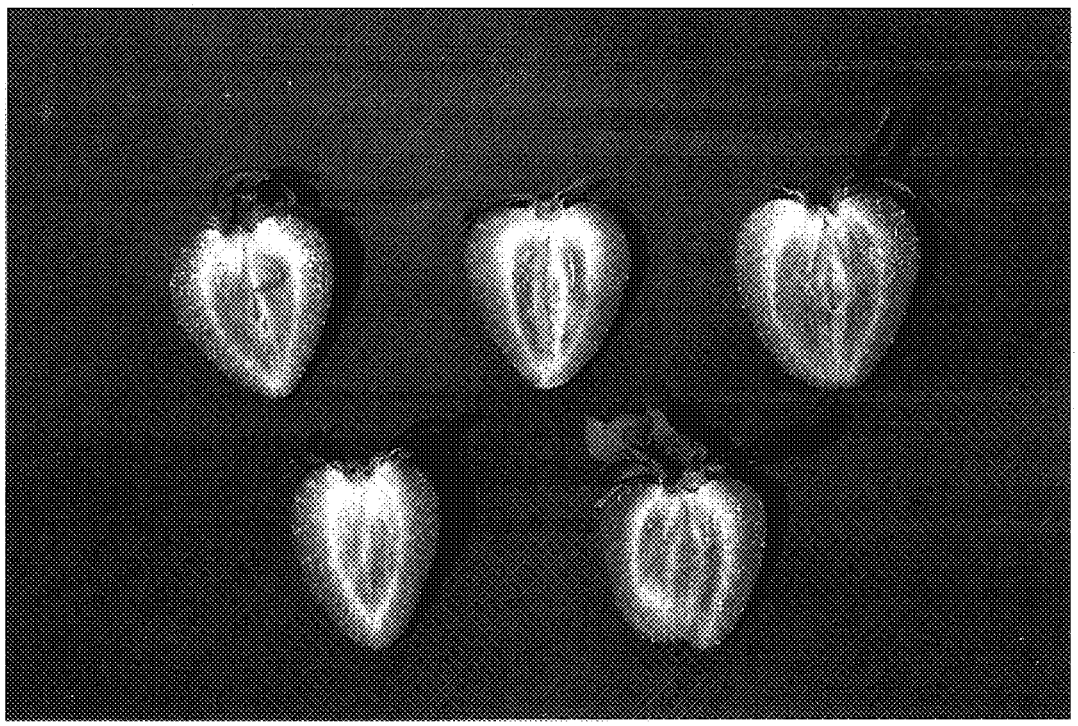
FIG. 5 shows the fruit in longitudinal cross-section.

The following detailed description of the new variety is based upon observations taken of plants harvested from a nursery in Bonanza, Oreg. in September and October, 2004 and held in cold storage until planting in Ventura County, Calif. in October, 2004. Plants were grown in raised beds of soil under conditions typical of commercial strawberry production in Ventura County, Calif. Fruits were harvested twice weekly from January, 2005 to May, 2005 for yield determination. Observations of 'Driscoll Ojai', 'Driscoll El Capitan', and 'Driscoll Venice' were made in side by side comparison in April, 2005. Color designations, color descriptions, and other phenotypical descriptions may deviate from the stated values and descriptions depending upon variation in environmental, seasonal, climatic and cultural conditions. Colors are described and the most similar color designations are provided from the Royal Horticultural Society (RHS) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2, 3 and 4. In the tables, the flowers described are secondary flowers except where indicated. The fruit described is the secondary fruit on seven months old plants. Fruit and flower measurements are an average of both primary and secondary fruit and flowers.

Table 1 provides information on the plant and fruit characteristics of the new variety 'Driscoll Ojai' compared with characteristics of 'Driscoll El Capitan' and 'Driscoll Venice'. Table 2 provides additional information of the plant and fruit characteristics of the new variety 'Driscoll Ojai' compared with characteristics of the varieties 'Driscoll El Capitan' and 'Driscoll Venice'. Table 3 provides reactions of the new variety to stresses, pests and diseases compared with reactions of the varieties 'Driscoll El Capitan' and 'Driscoll Venice'. Table 4 provides isozyme characteristics of the new variety as compared to that of the varieties 'Driscoll El Capitan' and 'Driscoll Venice'.

TABLE 1

QUANTITATIVE COMPARISON OF 'DRISCOLL OJAI', 'DRISCOLL EL CAPITAN' AND 'DRISCOLL VENICE'

| | 'Driscoll Ojai' | 'Driscoll El Capitan' | 'Driscoll Venice' |
|---|---|---|---|
| Plant Characteristics | | | |
| Height of Plant (cm) | 22.6 | 20.8 | 18.5 |
| Spread of Plant (cm) | 32.1 | 31.0 | 31.5 |
| Number of Crowns | 4.1 | 4.0 | 3.2 |
| Leaf Characteristics | | | |
| Terminal Leaflet Length (cm) | 7.4 | 6.7 | 6.3 |
| Terminal Leaflet Width (cm) | 7.0 | 6.0 | 6.5 |
| Terminal Leaflet Length/Width Ratio | 1.06 | 1.12 | 0.96 |
| # Teeth/Terminal Leaflet | 22.0 | 20.0 | 23.7 |
| Color of upper side | 137A medium green | 147A dark green | 147A dark green |
| Color of under side | 147D light to medium green | 147C light to medium green | 139C light to medium green |
| Petiole Length (cm) | 15.5 | 13.5 | 12.2 |
| Petiole Diameter (mm) | 3.0 | 3.1 | 3.5 |
| Petiole Color | 145C yellow green | 149A yellow green | 149A yellow green |
| Petiolule Length (mm) | 7.6 | 8.1 | 5.9 |
| Petiolule Diameter (mm) | 1.8 | 1.7 | 1.8 |
| Petiolule Color | 145B yellow green | 149A yellow green | 149A yellow green |
| Bract Frequency | 42% typically paired | 0% | 8% typically single |
| Stipule Length (cm) | 3.8 | 3.9 | 3.7 |
| Stipule Width (cm) | 0.94 | 0.93 | 0.95 |
| Stolon Characteristics | | | |
| Anthocyanin color | 61C purple red | 58A purple red | |
| Diameter at bract (mm) | 3.16 | 2.51 | |
| Avg. # of Daughter plants | 62 (2003 Nursery) | 61.8 (2002 Nursery) | 71 (2002 Nursery) |
| Flower Characteristics | | | |
| Petal Length (cm) | 1.28 | 1.31 | 1.40 |
| Petal Width (cm) | 1.23 | 1.28 | 1.32 |
| Petal Length/Width Ratio | 1.04 | 1.02 | 1.06 |
| Flower Diameter (cm) | 2.35 | 2.37 | 2.6 |
| Calyx Diameter (cm) | 4.3 | 4.24 | 4.94 |
| Sepal Length (mm) | 19.6 | 18.6 | 20.9 |
| Sepal Width (cm) | 9.49 | 8.33 | 9.67 |
| Color of Upper and Lower Surface of Petal | 155C white | 155C white | 155C white |
| Receptical Color | 1A yellow | 7A yellow | 7A yellow |
| Anther Color | 12A yellow | 13A yellow | 13A yellow |
| Fruiting Truss Length (cm) | 27.9 | 24.8 | 18.2 |
| Fruit Characteristics | | | |
| Fruit Length (cm) | 4.6 | 4.3 | 4.5 |
| Fruit Width (cm) | 3.7 | 3.3 | 4.2 |
| Fruit Length/Width Ratio | 1.27 | 1.32 | 1.06 |
| Average Berry Weight (g) | 26.8 | 26.3 | 30.6 |
| External Color | 46A dark red | 53A dark red | 45A medium red |
| Internal Color | 42B medium red | 43A red | 34A and 155C orange red and white |
| Achene Coloration | 59B to 9A dark red to yellow | 60A to 151A dark red to yellow green | 60A to 15B dark red to yellow |
| 2003 Marketable Yield (g/plant) | 712 | 661 | 592 |

TABLE 2

QUALITATIVE COMPARISON OF 'DRISCOLL OJAI', 'DRISCOLL EL CAPITAN' AND 'DRISCOLL VENICE'

| | 'Driscoll Ojai' | 'Driscoll El Capitan' | 'Driscoll Venice' |
|---|---|---|---|
| Plant | | | |
| Habit | globose | globose | globose |
| Canopy Density | open | medium dense | medium dense |
| Vigor | strong | medium | medium |
| Leaf | | | |
| Shape in cross section | concave | slightly concave | slightly concave |
| Interveinal blistering | strong | strong | strong |
| Glossiness | medium | strong | strong |
| Number of leaflets | three only | three only | three only |
| Terminal leaflet margin profile | crenate | crenate | crenate |
| Terminal leaflet shape of base | rounded | rounded | rounded |
| Terminal leaflet shape of teeth | obtuse | obtuse | obtuse |
| Stipule pubescence | medium | sparse to medium | medium |
| Petiole pubescence | dense | dense | dense |
| Petiole pose of hairs | outwards | outward to downward | outward to downward |
| Stolon | | | |
| Anthocyanin coloration | weak | medium to strong | medium |
| Thickness | medium | thin | medium |
| Pubescence | weak | sparse to medium | medium to dense |
| Inflorescence | | | |
| Position relative to foliage | above | above | level to above |
| Diameter of calyx relative to corolla on secondary flowers | larger | larger | larger |
| Diameter of inner calyx relative to outer on secondary flowers | larger | smaller to same size | smaller |
| Spacing of petals | touching | overlapping | touching to overlapping |
| Fruiting Truss | | | |
| Attitude at first picking | prostrate | prostrate | prostrate |
| Fruit | | | |
| Predominant shape | almost cylindrical | cordate | cordate |
| Difference in shapes between primary and secondary fruits | moderate | marked | slight |
| Band without achenes | narrow | very narrow | very narrow |
| Unevenness of surface | weak to medium | weak to medium | weak |
| Evenness of color | even | slightly uneven to even | slightly uneven to even |
| Glossiness | strong | strong | medium to strong |
| Insertion of achenes | level with surface | below to level with the surface | level with surface |
| Insertion of calyx | level | in a basin to level | level to set above |
| Pose of the calyx segments | spreading to reflexed | reflexed | reflexed |
| Size of calyx in relation to fruit on secondary fruit | same size to larger | larger | larger |
| Adherence of calyx | medium to strong | strong | strong |
| Firmness of flesh | firm | firm | medium |
| Evenness of flesh color | slightly uneven | even | uneven |
| Distribution of flesh color | marginal and central | marginal and central | only marginal |

TABLE 2-continued

QUALITATIVE COMPARISON OF 'DRISCOLL OJAI', 'DRISCOLL EL CAPITAN' AND 'DRISCOLL VENICE'

| | 'Driscoll Ojai' | 'Driscoll El Capitan' | 'Driscoll Venice' |
|---|---|---|---|
| Hollow center size | medium | large | small to medium |
| Sweetness | strong | strong | strong |
| Texture when tasted | fine to medium | fine | medium |
| Acidity | medium | medium | weak |
| Time of First Flowering After Planting in 2004 | mid-December | mid-December | late-December |
| Harvest Interval in 2005 | late January to late-May | late January to late-May | late January to late-May |
| Type of Bearing | partially ever-bearing | partially everbearing | partially everbearing |

REACTION TO STRESS, PESTS, AND DISEASE

TABLE 3

REACTIONS TO STRESS PESTS AND DISEASES FOR 'DRISCOLL OJAI', 'DRISCOLL EL CAPITAN' AND 'DRISCOLL VENICE'

| | 'Driscoll Ojai' | 'Driscoll El Capitan' | 'Driscoll Venice' |
|---|---|---|---|
| Reaction to Pests | | | |
| *Tetranychus urticae* | moderately resistant | moderately resistant | moderately resistant |
| *Lygus hesperus* | susceptible | susceptible | susceptible |
| Reaction To Diseases | | | |
| Botrytis fruit rot | moderately susceptible | moderately susceptible | moderately susceptible |
| Powdery mildew | moderately susceptible | moderately resistant | moderately resistant |
| *Verticillium* wilt | susceptible | susceptible | susceptible |
| Strawberry Mottle Virus | moderately resistant | moderately resistant | moderately resistant |
| *Xanthomonas fragariae* | moderately susceptible | moderately susceptible | moderately susceptible |

ISOZYME ANALYSIS

In addition to the morphological description above, the new cultivar 'Driscoll Ojai' has been analyzed to obtain an indication of its genetic makeup to provide further means for identifying the new variety and distinguishing it from other somewhat similar and/or related strawberry varieties. Specifically, leaf samples of 'Driscoll Ojai'. 'Driscoll El Capitan' and 'Driscoll Venice' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL OJAI', 'DRISCOLL EL CAPITAN' AND 'DRISCOLL VENICE'

| Locus | 'Driscoll Ojai' | 'Driscoll El Capitan' | 'Driscoll Venice' |
|---|---|---|---|
| PGI | A1 | A2 | A4 |
| LAP | B3 | B3 | B3 |
| PGM | C2 | C4 | C2 |

What is claimed:

1. A new and distinct variety of strawberry plant, substantially as shown and described.

* * * * *